(12) United States Patent
Besser

(10) Patent No.: US 10,786,203 B1
(45) Date of Patent: Sep. 29, 2020

(54) MEDICAL PATCH APPLICATOR DEVICE

(71) Applicant: Daniel M. Besser, Braham, MN (US)

(72) Inventor: Daniel M. Besser, Braham, MN (US)

( * ) Notice: Subject to any disclaimer, the term of this patent is extended or adjusted under 35 U.S.C. 154(b) by 340 days.

(21) Appl. No.: 15/883,227

(22) Filed: Jan. 30, 2018

(51) Int. Cl.
*A61F 13/00* (2006.01)
*A61B 5/00* (2006.01)

(52) U.S. Cl.
CPC .. *A61B 5/6833* (2013.01); *A61F 2013/00646* (2013.01)

(58) Field of Classification Search
CPC ......... A61F 2013/00646; A61B 5/6833; A61B 5/6835; A61M 2037/0023
See application file for complete search history.

(56) References Cited

U.S. PATENT DOCUMENTS

| 5,052,381 A * | 10/1991 | Gilbert | A61F 13/023 206/441 |
| 2008/0114298 A1* | 5/2008 | Cantor | A61M 37/0015 604/117 |
| 2008/0245381 A1* | 10/2008 | Iosilevich | A45D 34/04 132/200 |
| 2010/0222743 A1* | 9/2010 | Frederickson | A61B 17/205 604/136 |
| 2012/0184916 A1* | 7/2012 | Kobayashi | A61M 37/0015 604/180 |
| 2015/0246214 A1* | 9/2015 | Simmers | A61M 37/0015 604/506 |
| 2016/0213908 A1* | 7/2016 | McAllister | A61M 37/0015 |
| 2016/0325082 A1* | 11/2016 | Kato | A61M 37/0015 |
| 2016/0354589 A1* | 12/2016 | Kobayashi | A61M 37/0015 |
| 2017/0050010 A1* | 2/2017 | McAllister | A61M 37/0015 |
| 2018/0326193 A1* | 11/2018 | Kobayashi | A61M 37/0015 |
| 2019/0038884 A1* | 2/2019 | Roux | A61N 1/303 |

* cited by examiner

*Primary Examiner* — Matthew F Desanto
(74) *Attorney, Agent, or Firm* — Johnson and Phung; Thomas N. Phung

(57) ABSTRACT

A medical patch applicator device for easily and effectively applying medical patches on difficult to reach areas of a person's body. The medical patch applicator device includes an elongated semi-rigid patch support member for supporting a medical patch to be applied anywhere upon a user's body; and patch engagement members attached to the support member and to which the medical patch clings so that the user can effectively apply the medical patch without the medical patch bunching and crumpling up.

2 Claims, 2 Drawing Sheets

MEDICAL PATCH APPLICATOR DEVICE

BACKGROUND OF THE INVENTION

Field of the Invention

The present invention relates to applicators and more particularly pertains to a new medical patch applicator device for easily and effectively applying medical patches on difficult to reach areas of a person's body.

Description of the Prior Art

The use of applicators is known in the prior art. More specifically, applicators heretofore devised and utilized are known to consist basically of familiar, expected and obvious structural configurations, notwithstanding the myriad of designs encompassed by the crowded prior art which have been developed for the fulfillment of countless objectives and requirements.

The prior art includes a plate adhesively adhering a medical patch to the plate and pinching a pinch to peel the plate from the medical patch. While this device fulfills its respective, particular objective and requirements, the aforementioned patent does not disclose a new medical patch applicator device.

SUMMARY OF THE INVENTION

The general purpose of the present invention, which will be described subsequently in greater detail, is to provide a new medical patch applicator device which has many of the advantages of the applicators mentioned heretofore and many novel features that result in a new medical patch applicator device which is not anticipated, rendered obvious, suggested, or even implied by any of the prior art applicators, either alone or in any combination thereof. The present invention includes an elongated semi-rigid patch support member for supporting a medical patch to be applied anywhere upon a user's body; and patch engagement members attached to the support member and to which the medical patch clings so that the user can effectively apply the medical patch without the medical patch bunching and crumpling up. None of the prior art includes the combination of the elements of the present invention.

There has thus been outlined, rather broadly, the more important features of the medical patch applicator device in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

It is an object of the present invention to provide a new medical patch applicator device which has many of the advantages of the applicators mentioned heretofore and many novel features that result in a new medical patch applicator device which is not anticipated, rendered obvious, suggested, or even implied by any of the prior art applicators, either alone or in any combination thereof.

Still another object of the present invention is to provide a new medical patch applicator device for easily and effectively applying medical patches on difficult to reach areas of a person's body.

Still yet another object of the present invention is to provide a new medical patch applicator device that can be used over and over again without adding any adhesive to the applicator for supporting the medical patch.

Even still another object of the present invention is to provide a new medical patch applicator device that prevents medical patches from being crumbled upon application and allows those having limited range of motion with one's arm to be able to easily apply the medical patch on hard to reach of the person's body such as one's lower back.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

DETAILED DESCRIPTION OF THE INVENTION

Figure 1:
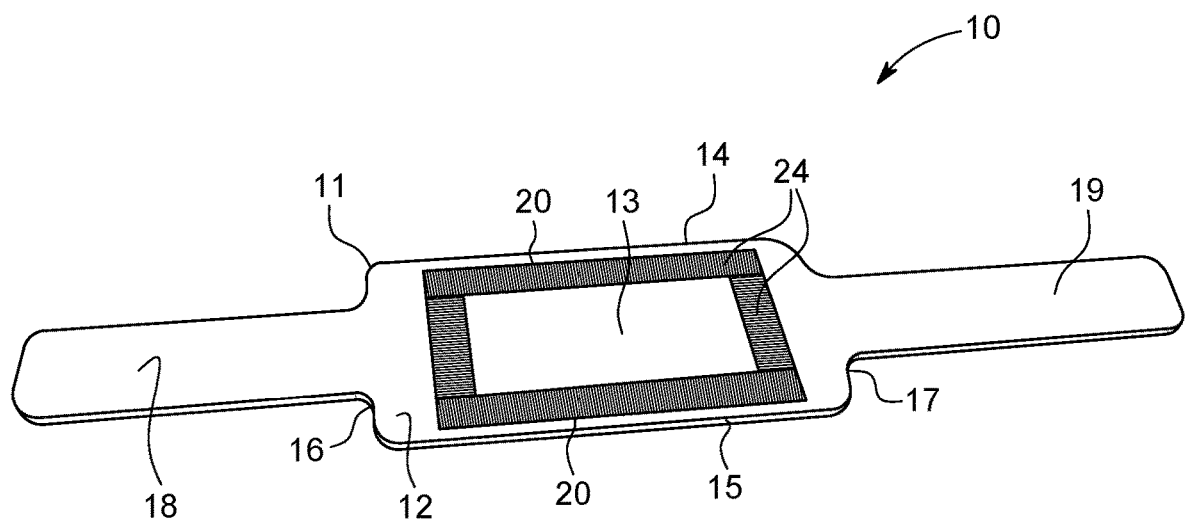
FIG. 1 is a perspective view of a new medical patch applicator device according to the present invention.
Figure 2:
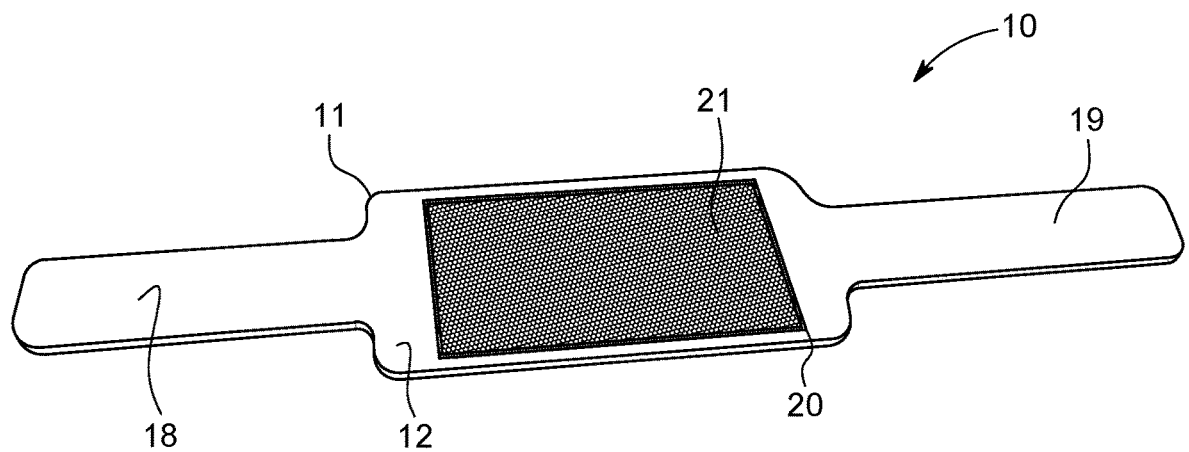
FIG. 2 is a perspective view of the present invention supporting the medical patch.
Figure 3:
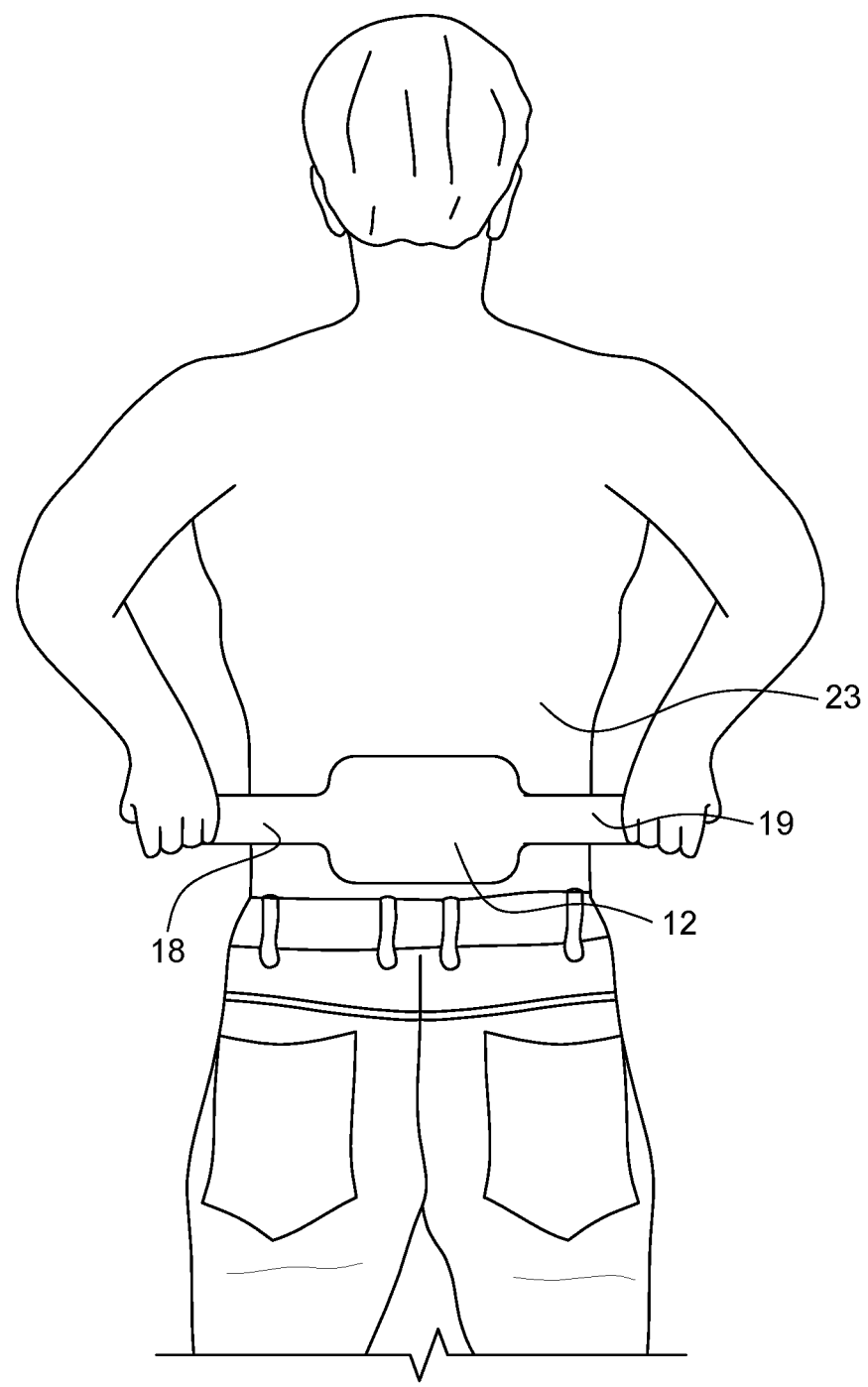
FIG. 3 is a perspective view of the present invention in use.

With reference now to the drawings, and in particular to FIGS. 1 through 3 thereof, a new medical patch applicator device embodying the principles and concepts of the present invention and generally designated by the reference numeral 10 will be described.

As best illustrated in FIGS. 1 through 3, the medical patch applicator device 10 generally comprises an elongated semi-rigid patch support member 11 for supporting a medical patch 21 to be applied anywhere upon a user's body 23; and patch engagement members 20 conventionally attached to the support member 11 and to which the medical patch 21 clings so that the user can effectively apply the medical patch 21 without the medical patch 21 bunching and crumpling up.

The patch support member 11 includes a planar main portion 12 which has a planar surface 13 and also has longitudinal side edges 14,15 and opposed end edges 16,17. The patch support member 11 also has elongated handle portions 18,19 each integrally and centrally attached to a respective end edge 16,17 and extending outwardly from the planar main portion 12. Each of the handle portions 18,19 has a length substantially equivalent to that of the main portion 12 for ease of use especially for applying the medical patch 21 to the user's back 23. Each of the handle portions 18,19 is planar and is longitudinally aligned with the main portion 12 and extends perpendicular to a respective end edge 16,17 of the main portion 12. The handle portions 18,19 lie in a plane with the main portion 12.

The engagement members 20 are strips of hook and loop fasteners conventionally attached to the planar surface 13 of the main portion 12. The strips of hook and loop fasteners 20 extend proximate to and along the side and end edges 14-17 of the main portion 12. The hook and loop fasteners 24 on the strips 20 face away from the planar surface 13 of the main portion 12 and removably engage and temporary support a back side of the medical patch 21.

In use, a back side of a medical patch 21 engages upon the patch engagement members 20 and a film protecting an adhesive side of the medical patch 21 is removed. The patch support member 11 is grasped and positioned over an area of a user's body 23 where the medical patch 21 is to be applied. The support member 11 is then pressed to the area of the user's body 23 with the medical patch 21 being applied to the user's body 23 and the patch engagement members 20 are disengaged from the medical patch 21 by removing the support member 11. The handle portions 18,19 are grasped with both hands of a user and the handle portions 18,19 are used to press the support member 11 to the user's body 23 and to disengage the patch engagement members 20 from the medical patch 21 by removing the support member 11 after applying the medical patch 21.

As a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing, is considered as illustrative only of the principles of the medical patch applicator device. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A method of using a medical patch applicator device comprising:

providing a patch support member having a main portion with side and end edges and a planar surface, and also includes opposed hand-grasping handle portions integrally extending from the end edges of the main portion and patch engagement members attached to the patch support member;

engaging a back side of a medical patch upon the patch engagement members and removing a film protecting an adhesive side of the medical patch;

grasping the patch support member and positioning the support member over an area of a user's body where the medical patch is to be applied; and grasping the handle portions with both hands of a user and using the handle portions to press the support member to the user's body and to disengage the patch engagement members from the medical patch by removing the support member after applying the medical patch.

2. The method of using the medical patch applicator device as described in claim 1, wherein the patch engagement members include strips of hook and loop fasteners attached proximate to and along the side and end edges of the main portion with the medical patch removably engaged to the hook and loop fasteners.

\* \* \* \* \*